United States Patent
Hu et al.

(10) Patent No.: US 6,291,721 B1
(45) Date of Patent: Sep. 18, 2001

(54) PROCESSES FOR THE PREPARATION OF 2-ARYLVINYL ALKYL ETHER AND 1,4-DIARYL-2-FLUORO-2-BUTENE COMPOUNDS

(75) Inventors: Yulin Hu, Plainsboro, NJ (US); David Allen Hunt, Newtown, PA (US); Weiguo Liu, Lawrenceville, NJ (US)

(73) Assignee: American Cyanamid Co., Madison, NJ (US)

( * ) Notice: Subject to any disclaimer, the term of this patent is extended or adjusted under 35 U.S.C. 154(b) by 0 days.

(21) Appl. No.: 09/373,262

(22) Filed: Aug. 12, 1999

(51) Int. Cl.[7] ............................. C07C 41/00; C07C 45/00
(52) U.S. Cl. ........................ 568/626; 568/426; 568/437; 568/559; 568/660; 568/661; 568/662; 568/663
(58) Field of Search ................................. 568/426, 437, 568/626, 659, 660, 661, 662, 663; 570/142, 143, 144

(56) References Cited

U.S. PATENT DOCUMENTS 5,998,673 * 12/1999 Barnes et al. .................. 568/634

FOREIGN PATENT DOCUMENTS

0881593 A1   10/1997   (EP)   ................. C07C/25/24

* cited by examiner

*Primary Examiner*—Rosalynd Keys
(74) *Attorney, Agent, or Firm*—Barbara V. Maurer

(57) ABSTRACT

An improved process for the preparation of 2-arylvinyl alkyl ether compounds of the structural formula I

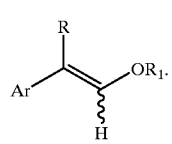

(I)

In addition, the present invention provides an improved process for the preparation of 1,4-diaryl-2-fluoro-2-butene compounds of the structural formula V

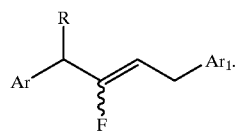

(V)

22 Claims, No Drawings

PROCESSES FOR THE PREPARATION OF 2-ARYLVINYL ALKYL ETHER AND 1,4-DIARYL-2-FLUORO-2-BUTENE COMPOUNDS

BACKGROUND OF THE INVENTION

2-Arylvinyl alkyl ether compounds, a method for their preparation, and their use as intermediates in the preparation of 1,4-diaryl-2-fluoro-2-butene insecticidal and acaricidal agents are described in EP 811593-A1. The method described in EP 811593-A1 for the preparation of 2-arylvinyl alkyl ether compounds requires the use of phosphonium halide compounds. However, this method is not entirely satisfactory because the required phosphonium halide compounds are relatively expensive and produce undesirable by-products which are difficult to remove from the 2-arylvinyl alkyl ether compounds. Accordingly, a need exists in the art for an improved process for the preparation of 2-arylvinyl alkyl ether compounds which avoids the use of phosphonium halide compounds.

It is, therefore, an object of the present invention to provide an improved process for the preparation of 2-arylvinyl alkyl ether compounds which avoids the use of phosphonium halide compounds.

It is also an object of the present invention to provide an improved process for the preparation of 1,4-diaryl-2-fluoro-2-butene compounds.

Other objects and advantages of the present invention will be apparent to those skilled in the art from the description below and the appended claims.

SUMMARY OF THE INVENTION

The present invention provides a new process for the preparation of 2-arylvinyl alkyl ether compounds of the structural formula I

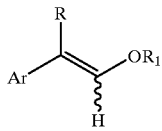

(I)

wherein
R is hydrogen, $C_1$–$C_4$alkyl, $C_1$–$C_4$haloalkyl, $C_3$–$C_6$cycloalkyl or $C_3$–$C_6$halocycloalkyl;
$R_1$ is $C_1$–$C_6$alkyl; and
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups,
 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
 a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups,
which process comprises:
(a) (1) reacting an aldehyde compound of the structural formula II

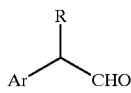

(II)

wherein R and Ar are as described above with an alkanol compound of the structural formula III $R_1OH$ (III)

wherein $R_1$ is as described above and a first acid to form an acetal compound of the structural formula IV

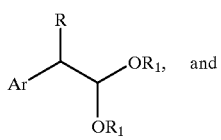

(IV)

(2) reacting the formula IV compound with a second acid in the presence of an aprotic solvent at an elevated temperature, or (b) reacting an aldehyde compound of the structural formula II

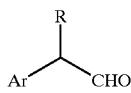

(II)

wherein R and Ar are as described above with an alkanol compound of the structural formula III $R_1OH$ (III)

wherein $R_1$ is as described above and a first acid in the presence of an aprotic solvent at an elevated temperature, or (c) reacting an acetal compound of the structural formula IV

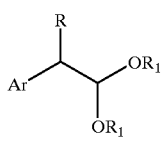

(IV)

wherein R, $R_1$ and Ar are as described above with a first acid in the presence of an aprotic solvent at an elevated temperature.

The present invention further provides a new process for the preparation of 1,4-diaryl-2-fluoro-2-butene compounds of the structural formula V (V)

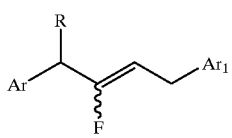

(I)

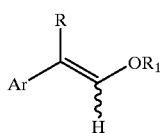

wherein

R is hydrogen, $C_1$–$C_4$alkyl, $C_1$–$C_4$haloalkyl, $C_3$–$C_6$cycloalkyl or $C_3$–$C_6$halocycloalkyl;

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups,
  1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
  a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and $Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
  phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
  a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, which process comprises the steps of:
  (a) preparing a 2-arylvinyl alkyl ether compound of the structural formula I wherein R and Ar are as described above and $R_1$ is $C_1$–$C_6$alkyl by:
  (1) reacting an aldehyde compound of the structural formula II (II)

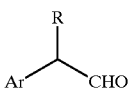

wherein R and Ar are as described above with an alkanol compound of the structural formula III $R_1OH$       (III)

wherein $R_1$ is as described above and a first acid to form an acetal compound of the structural formula IV (IV)

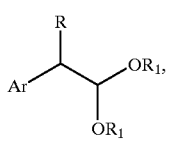

and reacting the formula IV compound with a second acid in the presence of an aprotic solvent at an elevated temperature, or (2) reacting an aldehyde compound of the structural formula II (II)

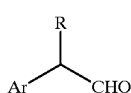

wherein R and Ar are as described above with an alkanol compound of the structural formula III $R_1OH$       (III)

wherein $R_1$ is as described above and a first acid in the presence of an aprotic solvent at an elevated temperature, or (3) reacting an acetal compound of the structural formula IV (IV)

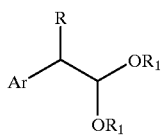

wherein R, $R_1$ and Ar are as described above with a first acid in the presence of an aprotic solvent at an elevated temperature;

(b) preparing a 3-aryl-2-fluoropropenal compound of the structural formula VI

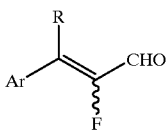
(VI)

wherein R and Ar are as described above by reacting the 2-arylvinyl alkyl ether compound with dichlorofluoromethane and a first base in the presence of water and optionally a phase transfer catalyst to form an intermediate compound, and reacting the intermediate compound in situ with water at an elevated temperature;

(c) preparing a 1,4-diaryl-2-fluoro-1,3-butadiene compound of the structural formula VII

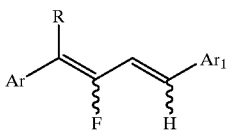
(VII)

wherein R, Ar and $Ar_1$ are as described above by:

(1) reacting the 3-aryl-2-fluoropropenal compound with an arylmethanesulfonyl fluoride or arylmethanephosphonate compound of the structural formula VIII

$Ar_1CH_2Y$ (VIII)

wherein Y is $SO_2F$ or $P(O)(OR_2)_2$, $R_2$ is $C_1$–$C_4$alkyl, and $Ar_1$ is as described above in the presence of a second base, or (2) reacting the 3-aryl-2-fluoropropenal compound with an arylmethanelithium compound of the structural formula IX

$Ar_1CH_2Li$ (IX)

wherein $Ar_1$ is as described above to form a 1,4-diaryl-2-fluoro-1-buten-3-ol compound of the structural formula X

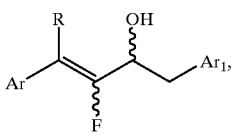
(X)

and reacting the formula X compound with a sulfonyl chloride or sulfonic acid anhydride compound and a third base, or (3) reacting the 3-aryl-2-fluoropropenal compound with an aryltriphenylphosphonium halide of the structural formula XI

$(C_6H_5)_3^+PCH_2Ar_1X^-$ (XI)

wherein X is Cl or Br and $Ar_1$ is as described above in the presence of a fourth base; and (d) reacting the 1,4-diaryl-2-fluoro-1,3-butadiene compound with: (1) an alkaline earth metal in the presence of a protic solvent, or (2) an alkali metal in the presence of an aprotic solvent.

DETAILED DESCRIPTION OF THE INVENTION

In a preferred embodiment of the present invention, the 2-arylvinyl alkyl ether compounds of formula I are prepared by reacting an aldehyde compound of formula II with an alkanol compound of formula III and an effective catalytic amount of a first acid in the presence of a solvent, preferably selected from the group consisting of the $R_1OH$ alkanol of formula III and an aprotic solvent and mixtures thereof, preferably with removal of the water generated in situ, to form an acetal compound of formula III, and reacting the formula III acetal compound with an effective catalytic amount of a second acid in the presence of an aprotic solvent at a temperature ranging from about 50° C. to 150° C., preferably 70° C. to 130° C., preferably with removal of the $R_1OH$ alkanol generated in situ.

In another preferred embodiment of this invention, the 2-arylvinyl alkyl ether compounds of formula I are prepared by reacting an aldehyde compound of formula II with an alkanol compound of formula III and an effective catalytic amount of a first acid in the presence of an aprotic solvent at a temperature ranging from about 50° C. to 150° C., preferably 70° C. to 130° C., preferably with removal of water and the $R_1OH$ alkanol from the reaction mixture.

The 2-arylvinyl alkyl ether compounds of formula I are also preferably prepared by reacting an acetal compound of formula IV with an effective catalytic amount of a first acid in the presence of an aprotic solvent at a temperature ranging from about 50° C. to 150° C., preferably 70° C. to 130° C., preferably with removal of the $R_1OH$ alkanol generated in situ.

Advantageously, the present invention provides processes for the preparation of 2-arylvinyl alkyl ether compounds which avoid the use of phosphonium halide compounds.

First and second acids suitable for use in the present invention include, but are not limited to, resin bound sulfonic acids such as the DOWEX® line of strongly acidic, cross-linked, ion-exchange resins (commercially available from Aldrich, Milwaukee, Wis.) and the like; sulfonic acids such as p-toluenesulfonic acid, and the like; mineral acids such as sulfuric acid, phosphoric acid, hydrogen chloride, and the like; and alkanoic acids such as acetic acid, propionic acid, and the like. Resin bound sulfonic acids and sulfonic acids are preferred first and second acids with sulfonic acids being more preferred. In a preferred embodiment of this invention, the first and second acids are the same.

The first and second acids are preferably present in an effective catalytic amount. The effective catalytic amount of the first or second acid is defined herein as any amount of the first or second acid which allows the reaction to proceed at lower reaction temperatures and/or shorter reaction times compared to the reaction temperatures and reaction times when the first or second acid is not present. Typically, this amount may be less than one molar equivalent per mole of the formula II aldehyde or formula IV acetal. The effective catalytic amount of the first or second acid is preferably about 0.001 to 1 molar equivalent per mole of the formula II aldehyde or formula IV acetal.

Aprotic solvents suitable for use in this invention include, but are not limited to, aromatic hydrocarbons such as toluene, benzene, xylenes, mesitylene, and the like; and halogenated aromatic hydrocarbons such as fluorobenzene, chlorobenzene, and the like. Preferred aprotic solvents include toluene and xylenes. In a preferred embodiment of the present invention, the aprotic solvent has a boiling point of greater than about 50° C.

3-Aryl-2-fluoropropenal compounds of formula VI are preferably prepared by reacting a 2-arylvinyl alkyl ether compound of formula I with dichlorofluoromethane or a dichlorofluoromethane equivalent and a base such as an alkali metal hydroxide in the presence of water and optionally a phase transfer catalyst such as a crown ether or a quaternary ammonium halide to form an intermediate compound, and reacting the intermediate compound in situ with water at an elevated temperature, preferably ranging from about 60° C. to 90° C.

In a preferred embodiment of the present invention, 1,4-diaryl-2-fluoro-1,3-butadiene compounds of formula VII are prepared by reacting a 3-aryl-2-fluoropropenal compound of formula VI with an arylmethanesulfonyl fluoride or arylmethanephosphonate compound of formula VIII and a base such as an alkali metal hydride, an alkali metal $C_1$–$C_6$alkoxide, an alkali metal hydroxide, an alkali metal carbonate, an alkaline earth metal hydroxide, an alkaline earth metal carbonate, a lithium base, a lithium dialkylamide, a lithium cyclicamide or a tri($C_1$–$C_6$alkyl) amine, optionally in the presence of a phase transfer catalyst such as a crown ether, a quaternary ammonium salt or a cryptand, preferably at a temperature ranging from about −78° C. to 150° C., more preferably from about −20° C. to about 100° C., in the presence of a solvent such as a carboxylic acid amide, an ether, a nitrile, a dialkylsulfoxide, an aromatic hydrocarbon or a $C_1$–$C_6$alcohol and mixtures thereof.

In another preferred embodiment of this invention, 1,4-diaryl-2-fluoro-1,3-butadiene compounds of formula VII are prepared by reacting a 3-aryl-2-fluoropropenal compound of formula VI with an arylmethanelithium compound of formula IX in the presence of an ether such as diethyl ether, tetrahydrofuran or 1,2-dimethoxyethane and mixtures thereof, preferably at a temperature ranging from about −78° C. to 30° C., to form a 1,4-diaryl-2-fluoro-1-buten-3-ol compound of formula X; and reacting the formula X compound with (a) a sulfonyl chloride such as an unsubstituted or substituted phenylsulfonyl chloride, a $C_1$–$C_6$alkylsulfonyl chloride or a $C_1$–$C_6$haloalkylsulfonyl chloride, or (b) a sulfonic acid anhydride such as an unsubstituted or substituted phenylsulfonic acid anhydride, a $C_1$–$C_6$alkylsulfonic acid anhydride or a $C_1$–$C_6$haloalkylsulfonic acid anhydride, and a base such as an alkali metal hydride, an alkaline earth metal hydride, an alkali metal $C_1$–$C_6$alkoxide, a $C_1$–$C_6$alkyllithium or a lithium dialkylamide, preferably at a temperature ranging from about −78° C. to 120° C., more preferably from about 20° C. to 80° C., in the presence of a solvent such as an ether, a carboxylic acid amide, a dialkyl sulfoxide, a nitrile, an aromatic hydrocarbon or a halogenated aromatic hydrocarbon and mixtures thereof.

1,4-Diaryl-2-fluoro-1,3-butadiene compounds of formula VII are also preferably prepared by reacting a 3-aryl-2-fluoropropenal compound of formula VI with an aryltriphenylphosphonium halide of formula XI in the presence of a base such as an alkali metal hydride, a $C_1$–$C_6$alkyllithium or a lithium dialkylamide.

1,4-Diaryl-2-fluoro-2-butene compounds of formula V are preferably prepared by reacting a 1,4-diaryl-2-fluoro-1,3-butadiene compound of formula VII with: (1) an alkaline earth metal such as magnesium or calcium in the presence of a protic solvent such as a $C_1$–$C_6$alcohol, or (2) an alkali metal such as lithium, sodium or potassium in the presence of an aprotic solvent such as ammonia or an ether.

Preferred formula I 2-arylvinyl alkyl ether compounds which may be prepared by the processes of this invention are those wherein R is $C_1$–$C_4$alkyl or $C_3$–$C_6$cycloalkyl;
$R_1$ is $C_1$–$C_3$alkyl; and
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups.

More preferred 2-arylvinyl alkyl ether compounds which may be prepared by the processes of this invention are those wherein R is isopropyl or cyclopropyl;
$R_1$ is $C_1$–$C_3$alkyl; and
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups.

Preferred formula V compounds which may be prepared by the processes of this invention are those wherein R is $C_1$–$C_4$alkyl or $C_3$–$C_6$cycloalkyl;
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and
$A_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups, 3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or 3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

More preferred 1,4-diaryl-2-fluoro-2-butene compounds which may be prepared by the processes of this invention are those wherein R is isopropyl or cyclopropyl;
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and
$Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

The present invention is especially useful for the preparation of

1-[1-(p-chlorophenyl)-2-methoxyvinyl]cyclopropane;
1-[1-(p-chlorophenyl)-2-isopropoxyvinyl]cyclopropane; and
1-[1-(p-chlorophenyl)-2-fluoro-4-(4-fluoro-3-phenoxyphenyl)-2-butenyl]cyclopropane.

In formulas I–XI above, the 5- and 6-membered heteroaromatic ring may suitably be a ring containing one to four heteroatoms selected from N, O and S, wherein the heteroatoms may be the same or different, e.g. the rings include, but are not limited to, pyridyl, pyrazolyl, imidazolyl, triazolyl, isoxazolyl, tetrazolyl, pyrazinyl, pyridazinyl, triazinyl, furanyl, thienyl and thiazolyl rings each optionally substituted as described in formulas I–XI above.

Exemplary of "halogen" hereinabove are fluorine, chlorine, bromine and iodine. The terms "$C_1$–$C_4$haloalkyl", "$C_3$–$C_6$halocycloalkyl" and "$C_1$–$C_4$haloalkoxy" are defined as a $C_1$–$C_4$alkyl group, a $C_3$–$C_6$cycloalkyl group and a $C_1$–$C_4$alkoxy group substituted with one or more halogen atoms, respectively, wherein the halogen atoms may be the same or different.

When used herein as a group or part of a group, the term "alkyl" includes straight or branched chain alkyl groups such as methyl, ethyl, n-propyl, isopropyl, n-butyl, isobutyl, s-butyl and t-butyl. When used herein as a group or part of a group, the term "cycloalkyl" includes cyclopropyl, cyclobutyl, cyclopentyl and cyclohexyl.

Groups containing two or more rings, such as phenoxyphenyl, phenoxypyridyl, biphenyl and benzylphenyl, which may be substituted, may be substituted on either ring unless otherwise specified herein.

Starting aldehyde compounds of formula II may be prepared using conventional procedures known in the art, see, e.g. U.S. Pat. No. 4,137,324; FR 2,348,919; and DE 2,717,414.

Arylmethanesulfonyl fluoride compounds of formula VIII wherein Y is $SO_2F$ may be prepared, as shown in Flow Diagram I, by reacting an arylmethanebromide compound of formula XII with sodium sulfite to form a sodium arylmethanesulfonate compound of formula XIII, reacting the formula XIII sulfonate compound with phosphorus pentachloride to form an arylmethanesulfonyl chloride compound of formula XIV, and reacting the sulfonyl chloride compound with potassium fluoride.

FLOW DIAGRAM I

Ar$_1$CH$_2$Br (XII)

Na$_2$SO$_3$

Ar$_1$CH$_2$SO$_2$Na (XIII)

PCl$_5$

Ar$_1$CH$_2$SO$_2$Cl (XIV)

KF

Ar$_1$CH$_2$SO$_2$F

Arylmethanephosphonate compounds of formula VIII wherein Y is $P(O)(OR_2)_2$ may be prepared, as shown in Flow Diagram II, by reacting an arylmethanebromide compound of formula XII with a tri($C_1$–$C_4$alkyl)phosphite compound of formula XV.

FLOW DIAGRAM II

Ar$_1$CH$_2$Br (XII)

P(OR$_2$)$_3$
(XV)

Ar$_1$CH$_2$P(O)(OR$_2$)$_2$

Alternatively, arylmethanephosphonate compounds of formula VIII wherein Y is $P(O)(OR_2)_2$ may be prepared, as shown in Flow Diagram III, by reacting an arylmethanebromide compound of formula XII with a di($C_1$–$C_4$alkyl)phosphite compound of formula XVI in the presence of a base such as an alkali metal $C_1$–$C_6$alkoxide.

FLOW DIAGRAM III

Ar$_1$CH$_2$Br (XII)

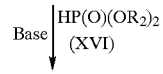Base  HP(O)(OR$_2$)$_2$
(XVI)

Ar$_1$CH$_2$P(O)(OR$_2$)$_2$

Arylmethanelithium compounds of formula IX may be prepared, as shown in Flow Diagram IV, by reacting an arylmethanebromide compound of formula XII with a lithium $C_1$–$C_6$alkyltellurolate compound in the presence of tellurium (Te) to form an intermediate compound of formula XVII, and reacting the intermediate compound with a $C_1$–$C_6$alkyllithium compound.

FLOW DIAGRAM IV

Ar$_1$CH$_2$Br (XII)

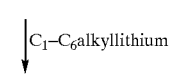Te  lithium  $C_1$–$C_6$alkyltellurolate

Ar$_1$CH$_2$TeLi (XVII)

$C_1$–$C_6$alkyllithium

ArCH$_2$Li (IX)

Aryltriphenylphosphonium halide compounds of formula XI may be prepared according to the procedures described in EP 811593-A1.

In order to facilitate a further understanding of this invention, the following examples are presented primarily for the purpose of illustrating more specific details thereof. The scope of the invention should not be deemed limited by the examples but encompasses the entire subject matter defined in the claims.

EXAMPLE 1

Preparation of 1-[1-p-Chlorophenyl)-2,2-dimethoxyethyl]cyclopropane

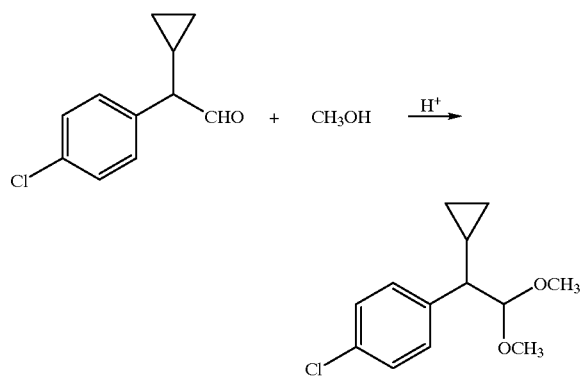

A solution of α-(p-chlorophenyl)-α-cyclopropane-acetaldehyde (1.0 g, 5.1 mmol) in methanol (5 mL) is slowly passed though a DOWEX® 50W-hydrogen, strongly acidic, 8% cross-linking, ion-exchange resin column at a flow rate of 1 mL/3 minutes. The column is then eluted with methanol. The passed solution is concentrated in vacuo to give the title product as an oil (1.2 g, 98% yield) which is identified by NMR spectral analyses.

EXAMPLE 2

Preparation of 1-[1-(p-Chlorophenyl)-2-methoxyvinyl]cyclopropane, (E)— and (Z)—

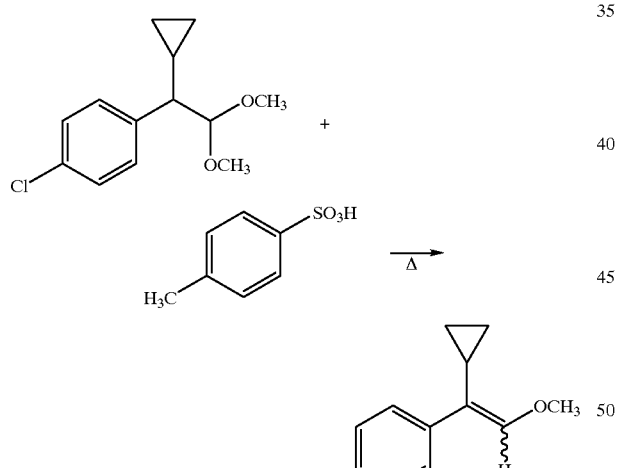

Water is azeotropically removed from a solution of p-toluenesulfonic acid monohydrate in toluene (150 g) until the distillate is clear. A solution of 1-[1-(p-chlorophenyl)-2,2-dimethoxyethyl]cyclopropane (24.7 g, 0.1 mol) in toluene is then added to the dried solution at 100° C. The resultant reaction mixture is refluxed for one hour, distilled to remove about 80 g of toluene/methanol, cooled to room temperature, treated with sodium carbonate (1 g), and poured into a saturated bicarbonate solution (100 mL). The organic phase is separated, washed with water, dried over anhydrous magnesium sulfate, and concentrated in vacuo to give the title product (20 g, 96% yield).

EXAMPLE 3

Preparation of 1-[1-(p-Chlorophenyl)-2-methoxyvinyl]cyclopropane, (E)— and (Z)—

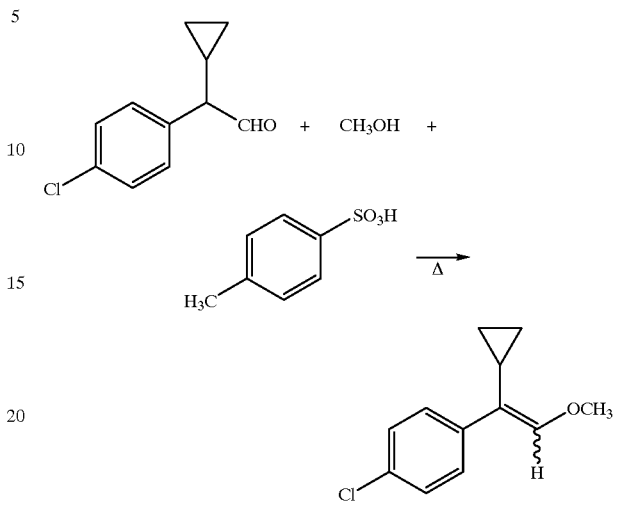

A mixture of α-(p-chlorophenyl)-α-cyclopropane-acetaldehyde (194.7 g), methanol (160 g), toluene (160 g) and p-toluenesulfonic acid (0.75 g) is refluxed for 10 minutes, distilled until the reaction mixture temperature reaches about 130° C., cooled to 60° C., diluted with toluene (160 g) and methanol (160 g), distilled until the reaction mixture temperature reaches about 130° C., cooled to 60° C., diluted with toluene (160 g) and methanol (160 g), distilled until the reaction mixture temperature reaches 145° C., cooled to 60° C., treated with sodium carbonate (1 g), stirred for 10 minutes, and poured into a saturated sodium carbonate solution (300 mL). The organic phase is separated, washed with water, dried over anhydrous sodium sulfate, and concentrated in vacuo to give the title product (204.2 g, 98% yield, isomer ratio 1:1.2).

EXAMPLE 4

Preparation of 1-[1-(p-Chlorophenyl)-2-isopropoxyvinyl]cyclopropane, (E)— and (Z)—

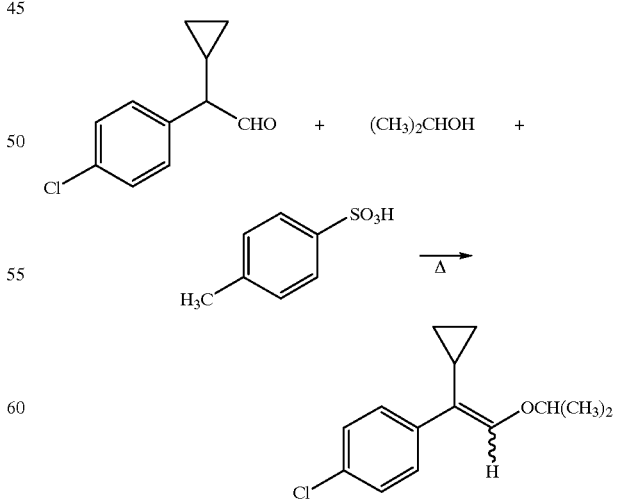

A mixture of α-(p-chlorophenyl)-α-cyclopropane-acetaldehyde (19.4 g), isopropanol (120 g) and p-toluenesulfonic acid (0.25 g) is refluxed for 15 minutes, distilled to remove 40 g of an isopropanol/water solution, treated with additional isopropanol (40 g), refluxed for 4 hours, distilled to remove 20 g of an isopropanol/water solution, treated with isopropanol (20 g), refluxed for 4 hours, treated with xylene, distilled at 105° C. to remove isopropanol/water, cooled to room temperature, washed with saturated sodium bicarbonate solution, and concentrated in vacuo to give the title product as a yellow oil (22 g, 93% yield, isomer ratio 1:1.2).

EXAMPLE 5

Following the procedures described in Examples 1–4, the following compounds are obtained:

| Z | R | $R_1$ |
|---|---|---|
| F | 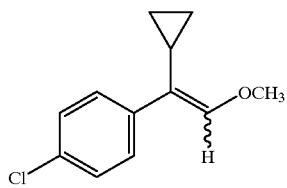 cyclopropyl | $CH_3$ |
| F | cyclopropyl | $CH(CH_3)_2$ |
| $OC_2H_5$ | cyclopropyl | $CH_3$ |
| $OC_2H_5$ | cyclopropyl | $CH(CH_3)_2$ |
| $CF_3$ | cyclopropyl | $CH_3$ |
| $CF_3$ | cyclopropyl | $CH(CH_3)_2$ |
| Cl | $CH(CH_3)_2$ | $CH_3$ |
| Cl | $CH(CH_3)_2$ | $CH(CH_3)_2$ |
| F | $CH(CH_3)_2$ | $CH_3$ |
| F | $CH(CH_3)_2$ | $CH(CH_3)_2$ |
| $OC_2H_5$ | $CH(CH_3)_2$ | $CH_3$ |
| $OC_2H_5$ | $CH(CH_3)_2$ | $CH(CH_3)_2$ |
| $CF_3$ | $CH(CH_3)_2$ | $CH_3$ |
| $CF_3$ | $CH(CH_3)_2$ | $CH(CH_3)_2$ |

EXAMPLE 6

Preparation of p-Chloro-β-cyclopropyl-α-fluorocinnamaldehyde

Procedure A

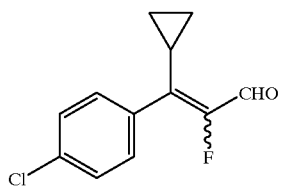

1) KOH/CHCl$_2$F/18-Crown-6
2) H$_2$O/Δ

A mixture of potassium hydroxide (3.37 g, 0.060 mol), 18-Crown-6 (0.087 g, 0.33 mmol) and 1-[1-(p-chlorophenyl)-2-methoxyvinyl]cyclopropane, (E)— and (Z)— (3.13 g, 0.015 mol) in water is treated with dichlorofluoromethane (8 g, 0.077 mol) at 7–10° C., stirred at 10–13° C. overnight, treated with additional dichlorofluoromethane (6 g, 0.058 mol) at 7–10° C., stirred at 10–13° C. for 36 hours, treated with water, stirred at 70–75° C. for 4 hours, cooled to room temperature, and extracted with ethyl acetate. The organic extracts are combined, washed sequentially with water, 2 N hydrochloric acid and water, dried over anhydrous sodium sulfate, and concentrated in vacuo to obtain a residue. Flash column chromatography of the residue using silica gel and an ethyl acetate/hexanes solution (1:9) gives 1.02 g of the E-isomer of the title product and 0.69 g of the Z-isomer of the title product (1.71 g total product).

Procedure B

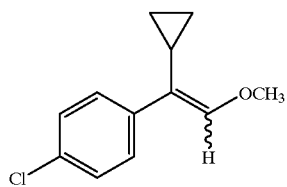

1) CHCl$_2$F/KOH/BTEAC
2) H$_2$O/Δ

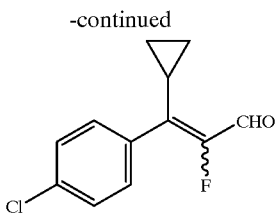

A mixture of 1-[1-(p-chlorophenyl)-2-methoxyvinyl] cyclopropane, (E)— and (Z)— (42 g, 0.2 mol) and benzyltriethylammonium chloride (1.0 g, 4.4 mmol) is treated with dichlorofluoromethane (62 g, 0.6 mol) at −5 to 0° C., treated with a 55% potassium hydroxide solution (122 g, 55%, 1.2 mol) over one hour at −5 to 20° C., and stirred at room temperature for 30 minutes. The pH of the resultant reaction mixture is adjusted to about pH 7 with a 5% acetic acid solution and the pH adjusted mixture is stirred at 70° C. for four hours and 80° C. for one hour. The resultant mixture is diluted with water and the phases are separated. The aqueous phase is extracted with methylene chloride and the organic extract is combined with the organic phase. The combined organic phase is washed sequentially with saturated sodium hydrogen carbonate solution and water, dried over anhydrous sodium sulfate, and concentrated in vacuo to give 40.4 g of the title product.

Using essentially the same procedures, the following compounds are obtained:

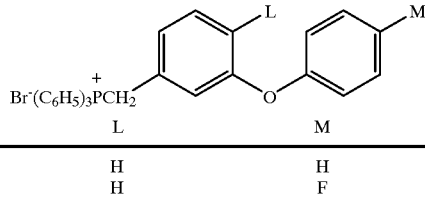

| Z | R |
|---|---|
| F | cyclopropyl |
| OC$_2$H$_5$ | cyclopropyl |
| CF$_3$ | cyclopropyl |
| Cl | CH(CH$_3$)$_2$ |
| F | CH(CH$_3$)$_2$ |
| OC$_2$H$_5$ | CH(CH$_3$)$_2$ |
| CF$_3$ | CH(CH$_3$)$_2$ |

EXAMPLE 7

Preparation of (4-Fluoro-3-phenoxybenzyl)triphenyl phosphonium bromide

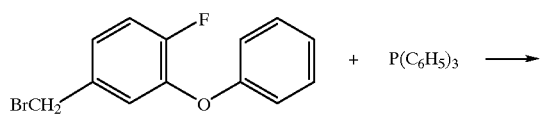 + P(C$_6$H$_5$)$_3$ ⟶

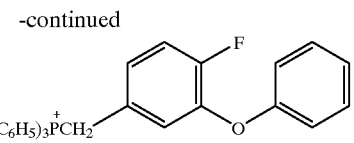

A solution of 4-fluoro-3-phenoxybenzyl bromide (42.17 g, 0.150 mol) in toluene is added to a solution of triphenyl phosphine (41.31 g, 0.158 mol) in toluene. The resultant reaction mixture is refluxed for one hour, cooled to room temperature, and filtered to obtain a solid. The solid is washed sequentially with toluene and hexanes, and dried in a dessicator at 60° C. to give the title product (73.7 g, 90.4%) which is identified by NMR spectral analyses.

Using essentially the same procedure, the following compounds are obtained:

| L | M |
|---|---|
| H | H |
| H | F |

EXAMPLE 8

Preparation of 1-(p-Chorophenyl)-1-cyclopropyl-2-fluoro-4-(4-fluoro-3-phenoxyphenyl)-1,3-butadiene

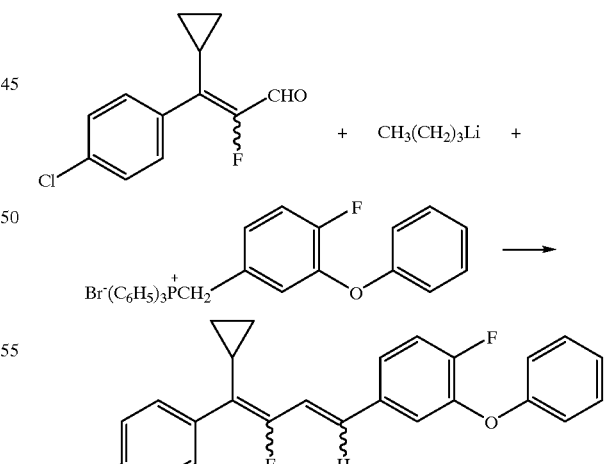

A mixture of (4-fluoro-3-phenoxybenzyl)triphenyl phosphonium bromide (41.77 g, 0.077 mol) in tetrahydrofuran is cooled to −55 to −60° C., treated dropwise with a 2.5 M solution of butyllithium in hexanes (32.15 mL, 0.080 mol), warmed to and stirred at room temperature for 2 hours, cooled ℀55 to −60° C., treated dropwise with a solution of 2-fluoro-3-cyclopropyl-3-(p-chlorophenyl)acrylaldehyde (15.7 g, 0.070 mol) in tetrahydrofuran, warmed to and stirred at room temperature overnight, and quenched with ethyl acetate and 2 N hydrochloric acid. The resultant aqueous mixture is extracted with ethyl acetate. The organic extracts are combined, washed sequentially with water, 2 N hydrochloric acid and water, dried over anhydrous sodium sulfate, and concentrated in vacuo to obtain a residue. Flash column chromatography of the residue using silica gel and an ethyl acetate/hexanes solution (1:9) gives the title product as an oil (26.0 g, 91%).

Using essentially the same procedure, the following compounds are obtained:

| Z | R | L | M |
|---|---|---|---|
| Cl | cyclopropyl | H | H |
| Cl | CH(CH$_3$)$_2$ | F | H |
| Cl | CH(CH$_3$)$_2$ | H | H |
| OC$_2$H$_5$ | CH(CH$_3$)$_2$ | F | H |
| OC$_2$H$_5$ | cyclopropyl | F | H |
| OC$_2$H$_5$ | CH(CH$_3$)$_2$ | H | H |
| OC$_2$H$_5$ | CH(CH$_3$)$_2$ | H | F |
| Cl | cyclopropyl | H | F |
| F | cyclopropyl | F | H |
| OC$_2$H$_5$ | cyclopropyl | H | H |
| F | cyclopropyl | H | H |
| F | CH(CH$_3$)$_2$ | F | H |

EXAMPLE 9

Preparation of 1-(p-Chlorophenyl)-1-cyclopropyl-2-fluoro-4-(4-fluoro-3-phenoxyphenyl)-1-buten-3-ol

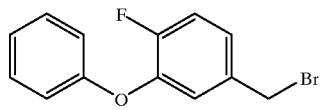

1) n-BuTeLi
2) n-BuLi

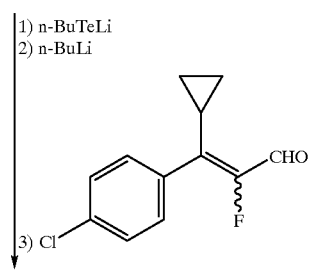

3) Cl

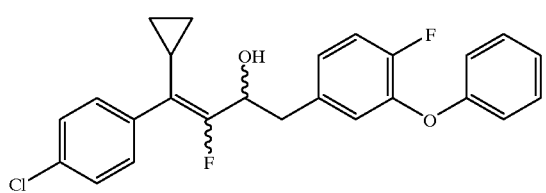

A solution of lithium n-butyltellurolate (10.5 mmol, n-BuTeLi), generated in situ from n-butyllithium (4.2 mL of 2.5 M solution in hexane, 10.5 mmol) and Te powder (1.34 g, 10.5 mmol) in tetrahydrofuran (10 mL) at 0° C., is treated with a solution of 3-phenoxy-4-fluorobenzyl bromide (2.81 g, 10 mmol) in tetrahydrofuran (10 mL) at 0° C., stirred for 30 minutes, cooled to −78° C., treated with a solution of n-butyllithium (4.2 mL of 2.5 M solution in hexane, 10.5 mmol), stirred for 30 minutes at −78° C., treated with a solution of p-chloro-β-cyclopropyl-α-fluorocinnamaldehyde (2.24 g, 10 mmol) in tetrahydrofuran (5 mL), warmed to room temperature with stirring for 3 hours, quenched with 2 N hydrochloric acid, and extracted with ethyl acetate. The combined organic extracts are washed with water, dried over anhydrous sodium sulfate, and concentrated in vacuo to obtain a residue. Flash chromatography of the residue on silica gel using a 1:4 ethyl acetate/hexanes solution gives the title product (3.5 g, 82% yield) which is identified by NMR spectral analyses.

Following essentially the same procedure, but using p-(trifluoromethyl)-β-cyclopropyl-α-fluorocinnamaldehyde, 1-(α,α,α-trifluoro-p-tolyl)-1-cyclopropyl-2-fluoro-4-(4-fluoro-3-phenoxyphenyl)-1-buten-3-ol is obtained.

EXAMPLE 10

Preparation of 1-(p-Chlorophenyl)-1-cyclopropyl-2-fluoro-4-(4-fluoro-3--phenoxyphenyl)-1,3-butadiene

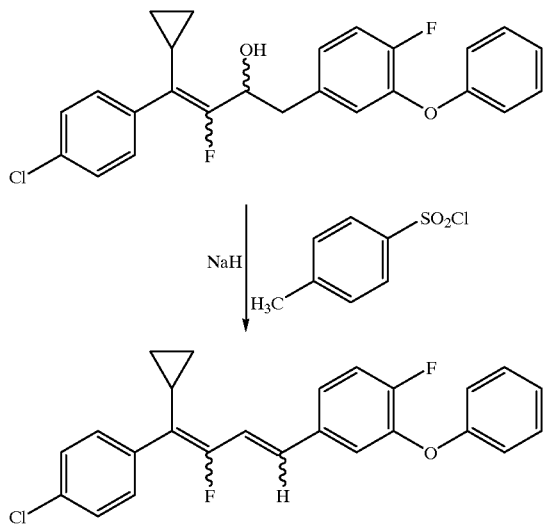

A suspension of sodium hydride (6.3 mg, 0.26 mmol) in tetrahydrofuran (1 mL) is treated with a solution of 1-(p-chlorophenyl)-1-cyclopropyl-2-fluoro-4-(4-fluoro-3-phenoxyphenyl)-1-buten-3-ol (106.7 mg, 0.25 mmol) in tetrahydrofuran (1.5 mL), stirred at 50° C. for 10 minutes, cooled to room temperature, treated with a solution of p-toluenesulfonyl chloride (49.6 mg, 0.26 mmol) in tetrahydrofuran (1 mL), stirred at 60° C. for 1 hour, quenched with water, and extracted with ethyl acetate. The combined organic extracts are washed sequentially with water, saturated sodium hydrogen carbonate solution and water, dried over anhydrous sodium sulfate, and concentrated in vacuo to obtain a residue. Flash chromatography of the residue using silica gel and a 1:9 ethyl acetate/hexanes solution gives the title product (62 mg, 61% yield) which is identified by NMR spectral analyses.

Following essentially the same procedure, but using 1-(α,α,α-trifluoro-p-tolyl)-1-cyclopropyl-2-fluoro-4-(4-fluoro-3-phenoxyphenyl)-1-buten-3-ol, 1-(α,α,α-trifluoro-p-tolyl)-1-cyclopropyl-2-fluoro-4-(4-fluoro-3-phenoxyphenyl)-1,3-butadiene is obtained.

EXAMPLE 11

Preparation of (4-Fluoro-3-phenoxyphenyl) methanesulfonyl fluoride

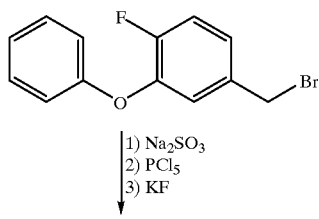

1) Na$_2$SO$_3$
2) PCl$_5$
3) KF

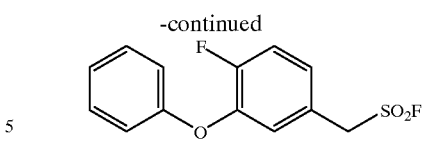

Step 1

A mixture of α-bromo-4-fluoro-3-phenoxytoluene (4.86 g, 17.3 mmol) and sodium sulfite (2.39 g, 19 mmol) in 50% aqueous methanol (20 mL) is heated at reflux for 5 hours and cooled to room temperature. The resultant colorless solid is collected by filtration and washed with chilled 50% aqueous methanol and methanol to obtain 3.4 g of sodium (4-fluoro-3-phenoxyphenyl)methanesulfonate. Another 1.8 g of product is recovered from the mother liquors.

Step 2

The sodium sulfonate obtained in step 1 is mixed with phosphorous pentachloride at room temperature for two days. An ice-water mixture is added and the aqueous solution is extracted with methylene chloride. The organic extract is washed with water, dried over anhydrous sodium sulfate, and concentrated in vacuo to obtain (4-fluoro-3-phenoxyphenyl)methanesulfonyl chloride as a syrup (2.05 g).

Step 3

The sulfonyl chloride obtained in step 2 (2.0 g, 6.65 mmol) is diluted with acetonitrile (20 mL). The resultant solution is treated with potassium fluoride (1.93 g, 33.25 mmol) and tetrabutylamonium fluoride (0.208 g, 0.66 mmol), stirred at room temperature for one day, poured into water, and extracted with ethyl acetate. The organic extract is washed with water, dried over anhydrous sodium sulfate, and concentrated in vacuo to obtain a residue. Flash chromatography of the residue on silica gel eluting with 15:85 ethyl acetate/hexanes gives (4-fluoro-3-phenoxyphenyl) methanesulfonyl fluoride (0.81 g, mp 59.5–61.5° C.) which is identified by NMR spectral analyses.

EXAMPLE 12

Preparation of 1-(p-Chlorophenyl)-1-cyclopropyl-2-fluoro-4-(4-fluoro-3-phenoxyphenyl)-1,3-butadiene

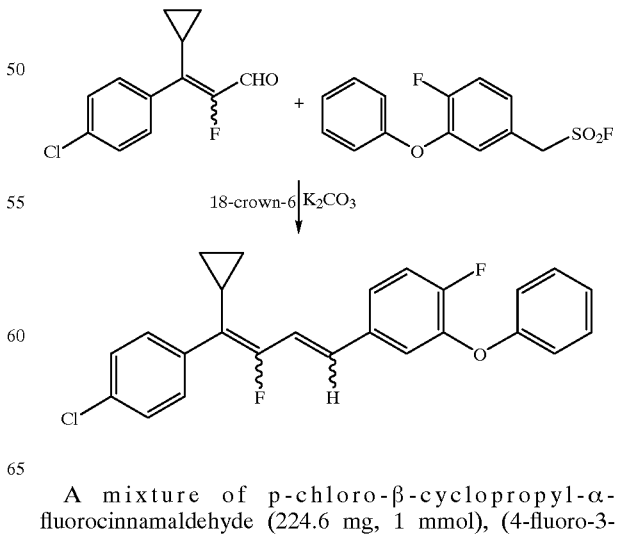

A mixture of p-chloro-β-cyclopropyl-α-fluorocinnamaldehyde (224.6 mg, 1 mmol), (4-fluoro-3- phenoxyphenyl)methanesulfonyl fluoride (312.7 mg, 1.1 mmol), potassium carbonate (552.8 mg, 4 mmol), and 18-crown-6 (13.2 mg, 0.05 mmol) in acetonitrile is stirred at room temperature overnight, quenched with water, and extracted with ethyl acetate. The organic extract is washed with water, dried over anhydrous sodium sulfate, and concentrated in vacuo to give the title product (380 mg, 94% pure by GC analysis, 93% yield) which is identified by NMR spectral analyses.

EXAMPLE 13

Preparation of Diethyl (4-fluoro-3-phenoxybenzyl) phosphonate

Procedure A

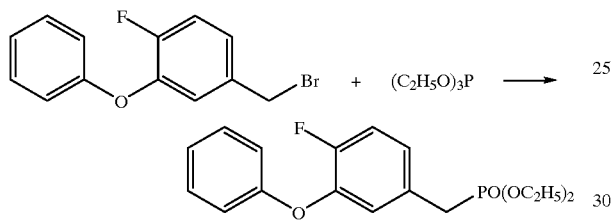

A mixture of 4-fluoro-3-phenoxybenzyl bromide (28.1 g, 100 mmol) and triethyl phosphite (18.27 g, 110 mmol) is heated at 90° C. for 30 minutes while allowing some low boiling materials to distill off. The resultant mixture is heated at 140° C. for 3.5 hours and distilled at 120° C./2 mmHg to give the title product as a syrup (32.1 g, 95% yield) which is identified by NMR spectral analyses.

Procedure B

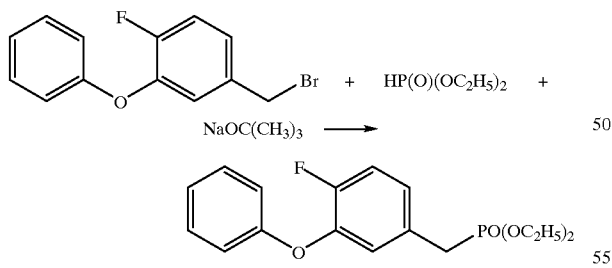

A mixture of diethylphosphite (6.9 g, 0.05 mol) in tetrahydrofuran is cooled to 10° C., treated portionwise with sodium t-butoxide (4.9 g, 0.05 mol) while maintaining the reaction mixture temperature below about 20° C., stirred at room temperature for 5 minutes, cooled, and treated dropwise with 4-fluoro-3-phenoxybenzyl bromide (14.05 g, 0.05 mol) at about 10–15° C. to give a solution of the title product in tetrahydrofuran (98% yield by gas chromatography).

EXAMPLE 14

Preparation of 1-(p-Chlorophenyl)-1-cyclopropyl-2-fluoro-4-(4-fluoro-3-phenoxyphenyl)-1,3-butadiene

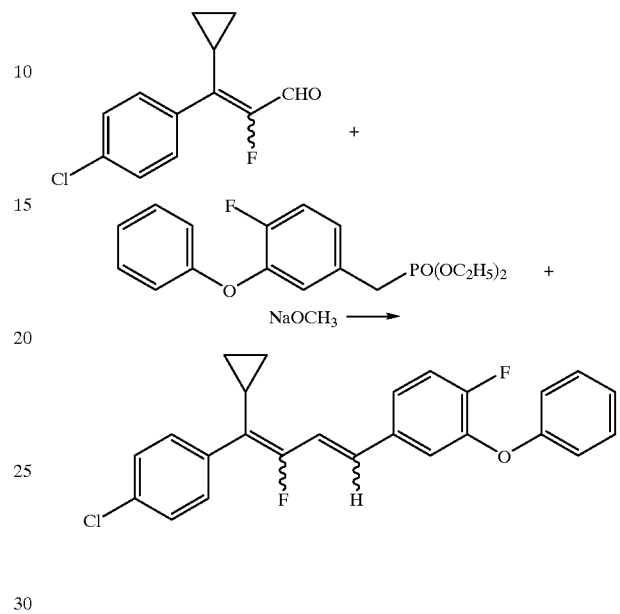

A stirred solution of diethyl (4-fluoro-3-phenoxybenzyl) phosphonate (2.64 g, 7.8 mmol) and p-chloro-β-cyclopropyl-α-fluorocinnamaldehyde (1.35 g, 6 mmol) in tetrahydrofuran (20 mL) is treated with sodium methoxide (562 mg, 9.36 mmol) at 0° C., stirred at room temperature overnight, quenched with 2 N aqueous hydrochloric acid, and extracted with ethyl acetate. The organic extract is washed sequentially with water, 2 N aqueous hydrochloric acid and water, dried over anhydrous sodium sulfate, and concentrated in vacuo to obtain a residue. Flash chromatography of the residue on silica gel eluting with 1:9 ethyl acetate/hexanes gives the title product as a syrup (2.15 g, 87.7% yield) which is identified by NMR spectral analyses.

EXAMPLE 15

Preparation of 1-[(1-(p-Chlorophenyl)-2-fluoro-4-(4-fluoro-3-phenoxyphenyl)-2-butenyl] cyclopropane, (R.S)—(Z)—

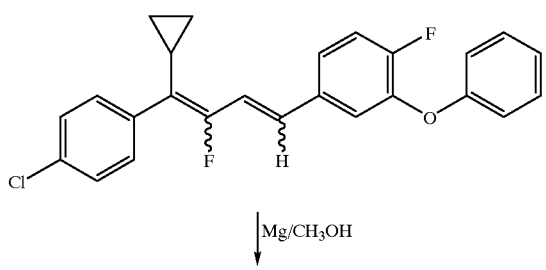

-continued

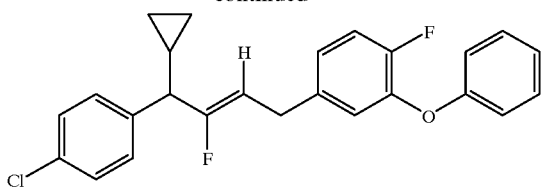

A solution of 1-(p-chlorophenyl)-1-cyclopropyl-2-fluoro-4-(4-fluoro-3-phenoxyphenyl)-1,3-butadiene (26 g, 0.064 mol) in a methanol/tetrahydrofuran solution (15:1) is treated with magnesium turnings (7.72 g, 0.317 mol), stirred at room temperature for 4 hours, quenched with hydrochloric acid, and extracted with ethyl acetate. The organic extracts are combined, washed sequentially with water, 2 N hdyrochloric acid and water, dried over anhydrous sodium sulfate, and concentrated in vacuo to obtain a residue. Flash column chromatography of the residue using silica gel and an ethyl acetate/hexanes solution (5:95) gives the title product as an oil (21.4 g, 82%) which is identified by NMR spectral analyses.

Using essentially the same procedure, the following compounds are obtained:

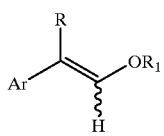

| Z | R | L | M |
|---|---|---|---|
| Cl | cyclopropyl | H | H |
| Cl | $CH(CH_3)_2$ | F | H |
| Cl | $CH(CH_3)_2$ | H | H |
| $OC_2H_5$ | $CH(CH_3)_2$ | F | H |
| $OC_2H_5$ | cyclopropyl | F | H |
| $OC_2H_5$ | $CH(CH_3)_2$ | H | H |
| $OC_2H_5$ | $CH(CH_3)_2$ | H | F |
| Cl | cyclopropyl | H | F |
| F | cyclopropyl | F | H |
| $OC_2H_5$ | cyclopropyl | H | H |
| F | cyclopropyl | H | H |
| F | $CH(CH_3)_2$ | F | H |
| $CF_3$ | cyclopropyl | F | H |

What is claimed is:

1. A process for the preparation of a 2-arylvinyl alkyl ether compound of the structural formula I $$\underset{Ar}{\overset{R}{\diagdown}}C=C\underset{H}{\overset{OR_1}{\diagup}} \quad (I)$$

wherein

R is hydrogen, $C_1$–$C_4$alkyl, $C_1$–$C_4$haloalkyl, $C_3$–$C_6$cycloalkyl or $C_3$–$C_6$halocycloalkyl;

$R_1$ is $C_1$–$C_6$alkyl; and

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups,
in the absence of phosphonuim halide compounds
which process comprises reacting a first acid with either:
(a) (1) an aldehyde compound of the structural formula II

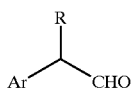

(II)

wherein R and Ar are as described above and an alkanol compound of the structural formula III $R_1OH$ (III)

wherein $R_1$ is as described above and a first acid, or
(b) an acetal compound of the structural formula IV

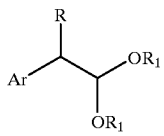

(IV)

in the presence of an aprotic solvent at an elevated temperature of from about 50° C. to about 150° C.

2. The process according to claim 1 wherein said first acid is selected from the group consisting of a resin bound sulfonic acid, a sulfonic acid, a mineral acid and an alkanoic acid.

3. The process according to claim 2 wherein said first acid is selected from the group consisting of a resin bound sulfonic acid and a sulfonic acid.

4. The process according to claim 3 wherein the acid is a sulfonic acid.

5. The process according to claim 4 wherein the sulfonic acid is p-toluenesulfonic acid.

6. The process according to claim 1 wherein the first acid is present in an effective catalytic amount.

7. The process according to claim 6 wherein the acid is present in the amount of about 0.001 to 1 molar equivalent per mole of the formula II aldehyde or formula IV acetal.

8. The process according to claim 1 wherein reactants II and III are used and water generated in situ during the reaction is removed from the reaction mixture.

9. The process according to claim 1 wherein reactant IV is used and $R_1OH$ alkanol generated in situ during the reaction is removed from the reaction mixture.

10. The process according to claim 1 wherein the aprotic solvent has a boiling point of greater than about 50° C.

11. The process according to claim 10 wherein the aprotic solvent is selected from the group consisting of an aromatic hydrocarbon and a halogenated aromatic hydrocarbon.

12. The process according to claim 11 wherein the aprotic solvent is selected from the group consisting of toluene and a xylene.

13. The process according to claim 1 wherein the elevated temperature is from about 70° C. to 130° C.

14. The process according to claim 1 wherein
R is $C_1$–$C_4$alkyl or $C_3$–$C_6$cycloalkyl;
$R_1$ is $C_1$–$C_3$alkyl; and
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups.

15. The process according to claim 14 wherein
R is isopropyl or cyclopropyl;
$R_1$ is $C_1$–$C_3$alkyl; and
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups.

16. A process according to claim 1, further comprising the steps of:
(a) preparing a 3-aryl-2-fluoropropenal compound of the structural formula VI

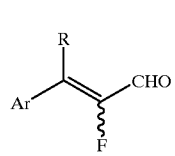

(VI)

wherein R and Ar are as described below by reacting the 2-arylvinyl alkyl ether compound of formula (I) with dichlorofluoromethane and a first base in the presence of water and optionally a phase transfer catalyst to form an intermediate compound, and reacting the intermediate compound in situ with water at an elevated temperature;

(b) preparing a 1,4-diaryl-2-fluoro-1,3-butadiene compound of the structural formula VII

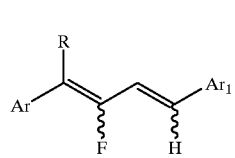

(VII)

wherein R, Ar and $Ar_1$ are as described below by:
(1) reacting the 3-aryl-2-fluoropropenal compound of formula (VI) with an arylmethanesulfonyl fluoride or arylmethanephosphonate compound of the structural formula VIII $Ar_1CH_2Y$ (VIII)

wherein Y is $SO_2F$ or $P(O)(OR_2)_2$, $R_2$ is $C_1$–$C_4$alkyl, and $Ar_1$ is as described below in the presence of a second base, or (2) reacting the 3-aryl-2-fluoropropenal compound with an arylmethanelithium compound of the structural formula IX $Ar_1CH_2Li$ (IX)

wherein $Ar_1$ is as described below to form a 1,4-diaryl-2-fluoro-1-buten-3-ol compound of the structural formula X

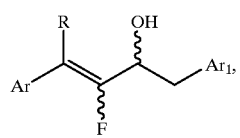

(X)

and reacting the formula X compound with a sulfonyl chloride or sulfonic acid anhydride compound and a third base, or (3) reacting the 3-aryl-2-fluoropropenal compound with an aryltriphenylphosphonium halide of the structural formula XI

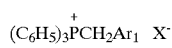  (XI)

wherein X is Cl or Br and $Ar_1$ is as described below in the presence of a fourth base; and (c) reacting the 1,4-diaryl-2-fluoro-1,3-butadiene compound of formula (VII) with: (1) an alkaline earth metal in the presence of a protic solvent, or (2) an alkali metal in the presence of an aprotic solvent, to form a 1,4-diaryl-2-fluoro-2-butene compound of the structural formula V

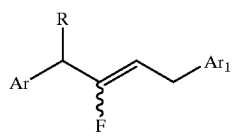  (V)

wherein

R is hydrogen, $C_1$–$C_4$alkyl, $C_1$–$C_4$haloalkyl, $C_3$–$C_6$cycloalkyl or $C_3$–$C_6$halocycloalkyl;

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and $Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups, phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups.

17. The process according to claim 1 wherein the compound of formula IV is prepared by reacting a first acid with a compound of formula II and a compound of formula III.

18. The process according to claim 1 wherein the compound of formula I is prepared by reacting a second acid with a compound of formula IV.

19. The process of claim 18 wherein said first and second acids are the same.

20. The process of claim 17 wherein said reaction for preparing the compound of formula IV is conducted in the presence of a solvent.

21. The process of claim 20 wherein the solvent is selected from the group consisting of the formula III compound, an aprotic solvent, and mixtures thereof.

22. The process of claim 17 wherein said second acid is selected from the group consisting of a resin bound sulfonic acid, a sulfonic acid, a mineral acid, and an alkanoic acid.

* * * * *